United States Patent [19]  
Franetzki

[11] 4,127,115  
[45] Nov. 28, 1978

[54] MEDICAL APPARATUS FOR THE MEASUREMENT OF RESPIRATORY FLOW INDEPENDENT OF GASEOUS COMPOSITION

[75] Inventor: Manfred Franetzki, Erlangen, Germany

[73] Assignee: Siemens Aktiengesellschaft, Berlin & Munich, Germany

[21] Appl. No.: 700,504

[22] Filed: Jun. 28, 1976

[30] Foreign Application Priority Data

Jul. 8, 1975 [DE] Fed. Rep. of Germany ....... 2530474

[51] Int. Cl.² .................................................. A61B 5/08
[52] U.S. Cl. .................................................. 128/2.08
[58] Field of Search ............. 128/2.07, 2.08, DIG. 17, 128/DIG. 29; 23/256; 73/211, 196, 205 R

[56] References Cited

U.S. PATENT DOCUMENTS

| 3,812,714 | 5/1974 | Olofsson et al. | 128/2.08 X |
| 3,857,385 | 12/1974 | Hampl | 128/2.08 |
| 4,022,193 | 5/1977 | Franetzki et al. | 128/2.08 |

Primary Examiner—Robert W. Michell
Assistant Examiner—Michael H. Thaler
Attorney, Agent, or Firm—Hill, Gross, Simpson, Van Santen, Steadman, Chiara & Simpson

[57] ABSTRACT

Respiratory flow rate is measured independent of gas type by establishing a supplementary flow component of the respiratory medium via a supplementary sensor modeled according to flow rate ratio after the primary respiratory flow sensor such that the sensors are subject to respective corresponding errors in dependence on the same parameter of any of the respective respiratory media. The respiratory flow signal is continuously corrected in dependency on the currently existent composition of the respiratory medium by forming the quotient of the respiratory flow signal and the supplementary signal from the supplementary sensor. In a second disclosed embodiment, the supplementary flow component is coupled to the primary respiratory flow sensor so that similitude is automatically provided. Either embodiment may be utilized to provide an inverse of the supplementary signal as a measure of a composition-dependent parameter such as viscosity, density or temperature coefficient of the respiratory gases.

14 Claims, 3 Drawing Figures

MEDICAL APPARATUS FOR THE MEASUREMENT OF RESPIRATORY FLOW INDEPENDENT OF GASEOUS COMPOSITION

CROSS REFERENCE TO RELATED APPLICATION

A continuing application is being filed on or about June 30, 1978, directed particularly to broader aspects of the embodiment of FIG. 1 of the present application.

BACKGROUND OF THE INVENTION

This invention relates to medical apparatus for the measurement, independent of gas type, of respiratory flow, having a breathing tube and a flow measurement sensor accommodated therein, for example a Fleisch pneumotachograph, a flow area restricting differential pressure type flowmeter, a thermal flowmeter, or the like.

Known devices for respiratory flow measurement operate, for example, with Fleisch pneumotachographs as respiratory flow receptors, such receptors being based on the principle that respiratory flow is subjected in the receptor to an effective flow resistance, the flow pressure being measured at two points, that is before and after the flow resistance. The pressure difference is proportional to the volume flow rate $\dot{V}$, with a proportionality factor containing geometrical apparatus constants and, further, parameters dependent on the gas type of the respiratory medium, for example the viscosity $\mu$. As a generalization, the signal output (S) from the usual flow measurement sensors can be expressed as a product of two functions, a flow function $f(\dot{V})$ and a parameter function $g(m_i)$, that is: $S = f(\dot{V}) \cdot g(m_i)$, where $M_i$ for example signifies one of the gas parameters: viscosity $\mu$, density $\rho$ and temperature conductivity $\lambda$. Other parameters are possible.

Because of the effect of the gas parameters, the range of application of the subject type of measurement apparatus has been limited. To be sure, the respiratory flow receptors can, by means of calibration with standard flows of a gas or also of a gas mixture of known composition, for example room air, be used for the measurement of the flow of the same respiratory gases with known composition. Such receptors are less suitable for the respiratory flow measurement of gases and gas mixtures of arbitrary or variable composition. The gas parameters must then, if necessary, be separately determined in special devices or be calculated for the respiratory gas mixture after a quantitative gas analysis, which can be very expensive. Thereafter, the result of the flow measurement must be corrected in accordance with the ascertained gas parameters. For the measurement of respiratory flow in connection with the evaluation of lung function by known techniques, such procedures are too expensive, considering the required exactness and speed of the measurement. It would indeed be desirable to carry out respiratory flow measurements with various respiratory gases at variable temperatures and partial pressures.

SUMMARY OF THE INVENTION

The invention thus has the underlying objective of eliminating this disadvantage. Medical apparatus of the type referred to at the outset is to be disclosed, which can be used for the measurement of respiratory flow with gases and gas mixtures of arbitrary or variable composition and temperatures, without the above named special devices and procedures being necessary to that end.

This objective is inventively accomplished in that, for the continuous correction of the measured values as a function of the composition and characteristics of the respiratory gases, the breathing tube has an auxiliary means comprising a pump, preferably an alternating pressure pump, which extracts a sample from the respiratory flow, and, if necessary, returns it thereto. The auxiliary means extracts such sample from the fluid medium of the breathing tube via a supplementary measurement sensor dependent on the same gas parameters and the measurement signal produced by such supplementary measurement sensor preferably has the same functional relationship to flow rate as the mesurement signal which is produced by the primary flow measurement sensor in the breathing tube. Further, means are provided for the formation of a respiratory flow indication which is a function of the quotient of the measurement signals obtained on the basis of the respiratory flow and of the supplementary flow produced by the auxiliary means. In such medical apparatus it is advantageous to make the supplemental measurement sensor smaller in accordance with the ratio of the supplementary sample flow to the respiratory flow, so that in the supplementary measurement sensor the same laws of fluid mechanics are valid as apply to the primary flow measurement sensor which senses the entire respiratory flow. The objective is further inventively accomplished in that, for the correction of the measurement values as a function of the composition and the characteristics of the respiratory gases, the breathing tube has auxiliary means comprising a pump, preferably an alternating pressure pump, which loads the respiratory flow with a defined supplementary flow component having a frequency which is capable of being differentiated from the breathing frequency, the supplementary flow component together with the respiratory flow being conveyed via the flow measurement sensor, and means being provided for the separation of, and for quotient formation as a function of, the low-frequency and high-frequency components of the measurement signals obtained on the basis of the combined presence of the respiratory flow and the supplemental flow component. It is advantageous in each instance if the supplementary flow impressed by the alternating pressure pump is a sinusoidal pulsation whose frequency is clearly above the breathing frequency.

Other objects, features and advantages of the present invention will be apparent from the following detailed description taken in connection with the accompanying sheet of drawing.

DETAILED DESCRIPTION

Figure 1:
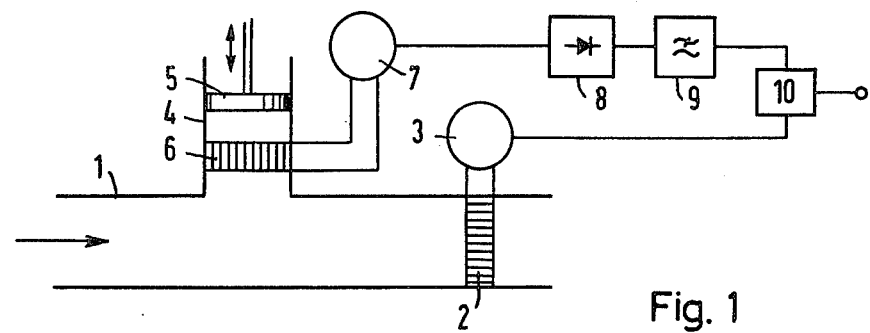
FIG. 1 is a schematic representation of a first exemplary embodiment of medical apparatus for respiratory flow measurement where the fluid medium within the apparatus may be made up of any arbitrary gas type, and where provision is made for the continuous correction of the effect of the viscosity of such fluid medium.

In FIG. 1 a breathing tube is designated with the reference numeral 1. This breathing tube has, at its end located opposite the mouthpiece (not shown), a respiratory flow receptor 2 which operates according to the principle of the Fleisch pneumotachograph. The tapped differential pressure $\Delta p$ which is generated as a function of flow in the breathing tube is converted by means of a transducer 3 into an analogous electrical signal (S). This signal (S) is proportional to the product of the viscosity $\mu$ and the volume flow ($\dot{V}$) to be measured. On the breathing tube there is additionally located an auxiliary duct 4 with an alternating pressure pump 5 (a diaphragm pump, for example, corresponding in its manner of actuation to a loudspeaker diaphragm, or a piston pump) and with a further respiratory flow receptor 6 which also operates according to the principle of the Fleisch pneumotachograph. With the alternating pressure pump 5 a small sample of known magnitude is periodically extracted from the fluid medium flowing in the breathing tube 1, the pump 5 preferably being operated according to a sinusoidal function with known frequency and producing at the receptor 6 a defined volume flow ($\dot{V}_1$), the pump extracting such supplementary flow component from the respiratory flow ($\dot{V}$) to be measured, the sample being extracted via the receptor 6 in one-half cycle of the pump operation and being returned again into the respiratory flow on the next half cycle. The receptor 6 is made smaller in accordance with the small sample ($\dot{V}_1$) to be extracted from the gas flow ($\dot{V}$), in comparison with the respiratory flow receptor 2, according to the laws of similitude of fluid mechanics. The measurement differential pressure signal $\Delta p_1$ is converted in the pressure transducer 7 into an analogous electrical signal ($S_1$) and, in the rectifier 8 with following low-pass filter 9, this analog signal is rectified and smoothed. The signal supplied by the low-pass filter 9 is proportional to the product of the known volume flow ($\dot{V}_1$) and the viscosity $\mu$. In the dividing component 10 which receives the signals (S) and ($S_1$), the quotient of the signals $S/S_1$ is formed. By the quotient formation $S/S_1$ the viscosity $\mu$ is eliminated and, since ($\dot{V}_1$) is known, a signal $S'$ dependent only on the volume flow $\dot{V}$ to be measured is obtained.

Figure 2:
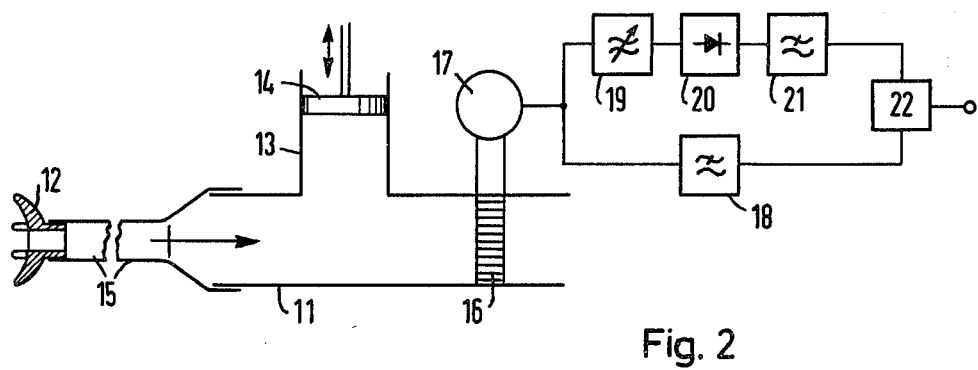
FIG. 2 is a schematic representation of a second exemplary embodiment.

In FIG. 2 the reference numeral 11 designates a flow measurement conduit, constructed as a breathing tube, with a test subject's mouthpiece 12 at one end for producing a respiratory flow $\dot{V}$. The breathing tube 11 in turn has an auxiliary duct 13 with an alternating pressure pump 14 which loads the breath flow $\dot{V}$ with a defined supplementary pulsation $\dot{V}_1$ which is at a higher frequency than the breathing frequency. Between the measurement tube 11 and the mouthpiece 12 there is located a longer hose 15 (for example with a length of nine hundred millimeters, 900 mm, and with an inside diameter of 12 millimeters, 12 mm) which hose represents an approximately purely inductive, sufficiently large flow resistance (for example, 1.5 millibars per liter per second, 1.5 mbar/l/s at a respiratory volume flow of 0.5 liter per second, $\dot{V} = 0.5$ l/s) and guarantees that the supplementary pulsation has a defined substantial effect on the flow measurement sensor 16. Further, the hose 15 prevents reactions of the impressed alternating supplementary flow component on the breathing pattern. At the open end of the breathing tube is situated the respiratory flow receptor 16 which is according to the principle of the Fleisch pneumotachograph. The differential pressure signal from receptor 16 is effected by a combination of the low-frequency respiratory flow $\dot{V}$ to be measured and the supplementary flow component which contains the known high-frequency volume flow pulsation $\dot{V}_1$. The analogous electrical signal $S_o$ formed at the output of the pressure transducer 17 thus contains low-frequency and high-frequency components. By a parallel connection of a low-pass filter 18 for transmitting the respiratory frequency and blocking the high-frequency component, and of a band-pass filter 19 tuned to the higher-frequency pulsation, a separation of the low-frequency and high-frequency components S and $S_1$ is achieved. The higher-frequency component $S_1$ is rectified and smoothed by means of rectifier 20 and subsequent low-pass filter 21. The low-frequency signal S is proportional to the product of viscosity $\mu$ and the volume flow $\dot{V}$ to be measured, while the smoothed signal $S_1$ is only dependent on the viscosity, since the supplementary volume flow component $\dot{V}_1$ is known and therefore only enters into the calculation in the form of a proportionality factor. By means of the quotient formation $S/S_1$ in the dividing component 22, a signal $S'$ which is dependent only on the volume flow $\dot{V}$ to be measured is then obtained. The proportionality factor is dependent on the magnitude of the pulsation of the alternating pressure pump 14 and can be calibrated into the apparatus to obtain a direct reading of respiratory flow $\dot{V}$ in liters per second.

Figure 3:
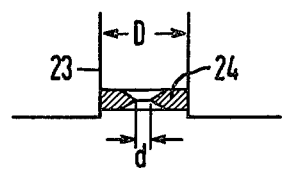
FIG. 3 is a schematic representation of a suitable flow orifice for the continuous correction of the effect of the density of the respiratory medium during the course of respiratory flow measurement.

Inventive devices for the respiratory flow measurement corrected for the effect of density $\rho$ and the temperature conductivity $\lambda$ are constructed in a correspondingly equivalent manner. As measuring sensors, then, flow orifices or Venturi tubes or, thermal flowmeters such as electrically energized temperature sensitive resistance elements, or pyroelectric elements are used. The orifice element 24, FIG. 3, is shown arranged in an auxiliary duct 23 which in one embodiment corresponds to the auxiliary duct 4 according to FIG. 1 and in another embodiment corresponds to the auxiliary duct 13 according to FIG. 2. For density compensation, the orifice element 24 must fulfill specific conditions as to its dimensioning in order to deliver a signal directly proportional to the density to the transducer 7 of FIG. 1 or the transducer 17 of FIG. 2. Thus applying FIG. 3 to the embodiment of FIG. 1, the supplementary flow component $\dot{V}_1$ produces a pressure differential across the orifice element 24, $\Delta p_1$ which is directly proportional to the density and is applied to the pressure transducer 7. In the embodiment of FIG. 3 according to FIG. 2, the signal $\dot{V}_1$ transmitted from the pump 14 via the orifice element 24 to the receptor 16 (or preferably a corresponding orifice) is used to generate a superimposed pressure differential signal $\Delta p_1$ which is directly proportional to the density of the fluid medium. Investigations have shown that, with a diameter D of the pump auxiliary duct 23 of 12 millimeters (D = 12 mm), the orifice element 24 with sharp edges and a diameter d of 2.2 millimeters (d = 2.2 mm) fulfills this requirement. The frequency of the alternating pressure pump 5 or 14 is at 15 hertz (15 Hz); the measuring time constant is at 200 milliseconds (200 ms) in each case.

The measurement signal magnitudes $S_i$ such as the signals S and $S_1$ referred to in connection with the exemplary embodiments of FIGS. 1 and 2, need not necessarily be directly proportional to the product of the influencing magnitudes or factors, such as for example, the viscosity $\mu$, density $\rho$ and the temperature conductivity $\lambda$, and the volume flow $\dot{V}$. More complicated functional dependencies corresponding to a signal structure $S = g(m_i) \cdot f(\dot{V})$, where $m_i$ signifies one of the possible gas parameters, are possible, which then require, in accordance with the known functions $g(m_i)$ and $f(\dot{V})$, a modification of the evaluation and calculating components. If the flow measurement sensors and the supplementary measurement sensors have different gas parameter functions $g_1(m_i)$ and $g_2(m_i)$, then these gas parameter functions must first be converted into a common gas parameter function $g(m_i)$ which may correspond to $g_1(m_i)$ or $g_2(m_i)$.

Such devices are generally applicable in gas flow measurement, in particular however in respiratory flow measurement with various test gases used in the lung function measurement technique, such as for example argon (Ar), Nitrogen ($N_2$), oxygen ($O_2$), carbon dioxide ($CO_2$), nitrous oxide ($N_2O$), helium ($H_e$), as well as water vapor ($H_2O$) and the mixtures thereof. The pulsation frequency of the alternating pressure pump is always to be not greater than about fifteen hertz ($f_1$ pump $\leq$ 15 Hz) and, in particular, is to be adjusted to the gases or, respectively, gas mixtures which are to be subject to the measurement techniques of the present invention. It must, however, be clearly separable technically from the breathing frequency. The achievable measurement accuracies lie near 2.5%. Further, with inventive devices of this type, measurements of other fluids, for example flowing liquids, can also be carried out. For this purpose, the correction of the flow measurements by the superimposition of an auxiliary or supplementary flow component operates in the sense of a continuous calibration.

In addition to the described respiratory flow and gas flow measurements it is also possible, with the inventive devices, to quickly and continuously determine the gas parameters themselves, whose effect was eliminated from the measurement signals in the continuous correction. By connecting an inverse-function-former after the low-pass filter 9 of FIG. 1 or, respectively, after the low-pass filter 21 of FIG. 2, the viscosity $\mu$ can be directly read off. Density $\rho$ and temperature conductivity $\lambda$ can be measured the same way using corresponding measurement sensors.

SUPPLEMENTAL DISCUSSION OF THE FEATURES OF THE ILLUSTRATED EMBODIMENTS

1. FIG. 1, and FIG. 3 as applied to duct 4 of FIG. 1, provide medical apparatus for the measurement of respiratory flow rate $\dot{V}(t)$, independent of the type of respiratory gas or gases making up the fluid medium within the apparatus. The flow measurement sensor 2 has been illustrated as a "Fleisch nozzle" in FIG. 1. (See, for example, the article "Der Pneumatoachograph" from "Neue Methoden zum Studium des Gasaustauches und der Lungenfunction" by A. Fleisch, VEB Thieme Leipzig, 1956). The flow measurement sensor 2 may also operate on the principle of throttled flow or on the principle of heat transfer fron an electrically-energized hot-wire flowmeter (that is, a temperature-sensitive rsistance element which thus may control electric current flow therethrough according to ambient gas flow rate), or the like. An important feature of such embodiments is characterized in that, for the continuous correction of the respiratory flow rate measurement signal from sensor 2, the breathing tube 1 has an axuiliary duct 4 or 23 connecting therewith with a pump, preferably an alternating pressure pump (such as 5), which extracts a sample from the respiratory flow at a suplementary flow rate $\dot{V}_1(t)$, and, if necessary, returns the sample thereto, and conveys the sample via a supplementary measurement sensor (such as receptor 6 or orifice element 24). The supplementary sensor is dependent on the same gas parameter ($m_1$) as affects the accuracy of the flow rate indication from the primary measurement sensor (such as receptor 2). The signal (such as $\Delta p_1$) from the supplementary mesurement sensor (6 or 24) preferably has the same functional relationship (operates on the same flowmetering principle) to flow rate $\dot{V}_1(t)$ as the signal (such as $\Delta p$) from the primary measurement sensor 2 has to its associated flow rate $\dot{V}(t)$. The supplementary means for continuously correcting the respiratory flow signal (S) includes further means (such as analog divider component 10) for forming the quotient ($S/S_1$) of the signals (S and $S_1$) obtained from the sensor 2 on the basis of respiratory flow $\dot{V}(t)$ and from the sensor 6 or 24 on the basis of supplementary flow component $\dot{V}_1$ as generated by the pump (such as 5).

2. A further characterizing feature of such embodiments of FIGS. 1 and 3 resides in that the sample extracted by the pump (such as pump 5 and via orifice 24 for the example of FIG. 3) producesa supplementary flow component $\dot{V}_1$ which is small in comparison to the respiratory flow component $\dot{V}$, and the supplemental measurement sensor (such as receptor 6 or 24) is made smaller in its significant physical dimensions according to the laws of dynamic similarity of fluid mechanics, in accordance with the ratio of supplementary flow $\dot{V}_1$ to respiratory flow $\dot{V}$. For the case where the pump such as 5 produces a sinusoidal supplementary flow component with a peak amplitude $\dot{V}_1$ (peak) and the sensor 2 responds to a maximum amplitude of respiratory flow of $\dot{V}$ (max), the revelant ratio for purposes of the laws of similitude of fluid mechanics may be taken as $\dot{V}_1$ (peak) / $\dot{V}$ (max). By way of example, the ratio $\dot{V}_1$ (peak) / $\dot{V}$ (max) may be less than one-tenth.

3. FIG. 2 and FIG. 3 as applied to duct 13 of FIG. 2 also illustrate medical apparatus for the sensing of respiratory flow rate $\dot{V}$ as a continuous function of time, using a Fleisch pneumotachograph, a sensor based on throttled flow (for example a Venturi), a thermal flowmeter (for example a hot-wire flowmeter), or the like. An important feature of these embodiments is characterized in that, for the continuous correction of the respiratory flow rate signal $S(t)$ which is produced under the control of sensor 16 as a function of the composition and the characteristics of the respiratory gas or gases making up the fluid medium within the apparatus, the breathing tube 11 has auxiliary means (such as 13, 14; and also orifice 24 for FIG. 3) including a pump, preferably an alternating pressure pump (such as 14), which loads the respiratory flow $\dot{V}(t)$ with a supplementary flow $\dot{V}_1$ having a supplementary flow component with a frequency which is capable of being differentiated from the breathing frequency, the supplementary flow component together with the respiratory flow $\dot{V}(t)$ being coupled with the flow measurement sensor 16, so that the supplementary signal $S_1(t)$ and the respiratory flow signal $S(t)$ are both dependent on a parameter ($m_1$) of a given fluid medium which affects the accuracy of the signal $S(t)$ as a measure of respiratory flow rate $\dot{V}(t)$. By way of example, with the illustrated embodiments, the signal $S(t)$ may deviate from the correct value because of differences in viscosity (for FIG. 2) or density (as to FIG. 3) for respective respiratory gas compositions such as argon, nitrogen, oxygen, carbon dioxide, nitrous oxide, helium, water vapor and the mixtures thereof, by an amount substantially exceeding plus or minus 2 5/10 percent. Supplementary measurement means (such as 18, 19 and 22) are present for separation of the composite signal $S_o(t)$ into low-frequency and high-frequency components $S(t)$ and $S_1(t)$, where the signal $S_o(t)$ is obtained on the basis of the mixture or superimposition of the respiratory flow $\dot{V}(t)$ and the supplementary flow $\dot{V}_1(t)$. The supplementary measurement means includes further means (such as analog divider component 22) for the formation of the quotient $S(t)/S_1(t)$ as a continuous function of time, thereby to provide a respiratory flow indication $S'(t)$ at the output of the further quotient formation means which is substantially continuously compensated for the parameter $(m_i)$ of the fluid medium substantially independently of the type of respiratory gas or gases making up the fluid medium.

4. With either the embodiment of FIG. 1 or FIG. 2 or either embodiment combined with FIG. 3, a further feature is characterized in that the supplementary flow $\dot{V}_1(t)$ produced by the alternating pressure pump (such as 5 or 14) is the result of a sinusoidal pulsation at an impressed frequency lying clearly above the breathing frequency. Preferably such impressed frequency is substantially higher than the highest anticipated breathing frequency (corresponding to the respiratory rate), and preferably such impressed frequency is between about 5 hertz and about 15 hertz.

5. In an embodiment such as illustrated in FIG. 2, or FIG. 3 taken with FIG. 2, where a substantial amplitude of the supplementary flow component $\dot{V}_1$ is to be present in the respiratory flow tube (such as breathing tube 11), a further feature is characterized in that between the respiratory flow tube and the patient's mouthpiece 12, a sufficiently large pneumatic flow resistance is arranged, preferably a hose line (such as 15) which is of substantial length and which presents a substantial (e.g. reactive) flow resistance. The flow resistance is preferably sufficiently large so that the supplementary flow component $\dot{V}_1$ has a substantial effect at the flow measurement sensor; and/or so that such flow resistance prevents perceptible effects at the mouthpiece 12 due to the supplementary flow component, such as might otherwise disturb the patient or cause the patient to alter his breathing pattern.

6. In conjunction with any of the foregoing features, the apparatus is further characterized in that for the evaluation of the time-continuous measuring signals (such as $\Delta p$ and $\Delta p_1$, FIG. 1), a measurement transducer (such as 3, 7, or 17) is provided for each such signal, so as to convert the time-continuous measuring signals supplied by the flow measurement sensors (such as 2, 6, 16 and 24) into respective analogous (analog) electrical signals which control the respective time-continuous analog electrical signals (such as S, $S_1$, FIG. 1; and $S_o$, FIG. 2) supplied to the supplementary measurement means (10, FIG. 1; and 18–22, FIG. 2.). In FIG. 1, the signal $S_1$ supplied to divider 10 is not identical to the output signal from transducer 7, but is nevertheless controlled thereby; the same terminology being applicable to an identical signal at the input and output ends of a single conductor, or example.

7. A further feature applicable to FIG. 2, and FIG. 3 taken with FIG. 2, is characterized in that, for the separation of the low-frequency and high-frequency components $S(t)$ and $S_1(t)$ of the composite electrical signal $S_o(t)$, electronic filter means are used, preferably a band-pass filter (such as 19) tuned to the pulsation frequency of the alternating pressure pump and a low-pass filter (such as 18) for the transmission of the breathing frequency component of signal $S_o(t)$.

8. As shown in FIGS. 1 and 2, the higher frequency component from transducers 7 to 17 is rectified by component 8 or 20 and smoothed in a low-pass filter component 9 or 21 to supply a time-continuous analog signal $S_1(t)$ which is proportional to the peak amplitude of the sinusoidal signal $\dot{V}_1$ supplied to the transducer 7 or 17, which has a constant known value, and the signal $g_1(m_i)$ which is a function of the gas parameter $(m_i)$ of the particular respiratory fluid medium.

9. With respect to any of the embodiments, the formation of the quotient $S(t)/S_1(t)$ is accomplished by electronic divider components (10, 22) such that the respiratory flow indication $S'$ is substantially continuously corrected with reference to any changes in the effect of parameter $(m_i)$. If the function $g_1(m_i)$ is not linearly related to the function $g(m_i)$ applying at receptor 2 in FIG. 1, or the similar embodiment as taught by FIG. 3, then $g_1(m_i)$ can be operated upon as part of the output of low-pass component 9 to generate the signal $S_1(t)$ which is a function of the product of $\dot{V}_1$ (peak) and $g(m_i)$.

10. With respect to the foregoing feature No. 9, if need be electronic calculating components may perform a conversion of the parameter function $\dot{V}_1 \cdot g_1(m_i)$ of the supplemental measurement sensor 6 into the function $S_2(t)$ which is linearly related to the parameter function $g(m_i)$ such that the respiratory flow indication $S' = S/S_2$ is formed by the quotient of $\dot{V}(t) \cdot g(m_i)$ and $k \cdot g(m_i)$, where k is a constant, the inaccuracy introduced by the parameter function $g(m_i)$, for example the viscosity function $g(\mu j)$, the density function $g(\rho j)$, and / or the temperature conductivity function $g(\lambda j)$ dependent on the composition of the respiratory medium (j), thus being essentially eliminated to give a measurement accuracy such as previously mentioned.

11. Medical apparatus is also envisioned for measuring parameters of the mentioned respiratory gases and also of other fluids, for example flowing liquids, utilizing a flow measurement sensor or sensors as in FIGS. 1, 2, or 1 or 2 as modified by FIG. 3, for example using one or more Fleisch pneumotochographs; one or more throttled flow devices (e.g. orifice plates or Venturi tubes); or one or more thermal flowmeters (e.g. hot-wire flowmeters); or the like. Such embodiments are characterized in that, for the rapid and continuous measurement and display and/or recording of the parameters $(m_{ij})$ of fluid media $(j_1, j_2, j_3, \ldots,$ etc.), for example viscosity $\mu$, density $\rho$, and temperature conductivity $\lambda$, which parameters are dependent on the composition of the fluid medium, there are provided supplementary measurement means coupled with the output of component 9 or 21, for the formation of the inverse function $1/S_1(t)$ where $S_1(t)$ is a function of the known constant $\dot{V}_1$ (peak) and $g(m_{ij})$, $g(m_{ij})$ being an inverse function of $(m_{ij})$ since increased viscosity, density or temperature conductivity, for example would result in a reduced signal to tranducer 7 or 17.

12. From the method standpoint, a feature of FIG. 1 resides in extracting a sample from the respiratory fluid medium of such magnitude and at such a rate that the respiratory flow is still properly measurable to provide a function $S(t)$ but is subject to an inaccuracy in proportion to a parameter function $g(m_{ij})$ for respective fluid composition (j), and utilizng the extracted sample to generate a signal $S_1$ as a measure of the parameter function $g_1(m_{ij})$ such that the parameter $(m_{ij})$ may itself be displayed or stored, or may be utilized to correct the function $S(t)$ for such inacuracy. By way of example, the extracted flow rate may be sensed by means of a supplementary sensor modeled by the principles of dynamic similarity after the primary sensor which generates signal $S(t)$ to generate a parameter function $g_1(m_{ij})$ which bears a predetermined relationship to $g(m_{ij})$ for each of a set of fluid media compositions $(j_1, j_2, j_3 \ldots,$ etc.) such that $g_1(m_{ij})$ can be converted to $g(m_{ij})$ with substantial accuracy for any member of the set $(ij)$. Preferably the value $g_1(m_{ij})$ is sensed anew in each cycle of the supplementary flow component $\dot{V}_1$ so that the correction function $g(m_{ij})$ is available for essentially continuous correction of the signal $S(t)$ representing the measured respiratory flow; that is the rate of correction of $S(t)$ may be at least several times the basic maximum respiratory rate of say 1 hertz, and preferably at least five times such basic maximum rate, such rate of supplementation in each case being such that for practical purposes of accuracy of the respiratory flow rates the correction may be considered to be continuous.

The foregoing features have been given by way of example, and without an intention to exhaustively list all important features; furthermore, the features have been discussed having reference to the illustrated embodiments for the sake of ease of explanation and it will be understood that many equivalent means and steps of implementation will occur to those skilled in the art from a consideration of this disclosure taken in its entirety.

While there have been disclosed exemplary embodiments representing presently preferred practice of the claimed invention, it will be apparent that many modifications and variations may be effected without departing from the scope of the novel teachings and concepts of the present invention.

I claim as my invention:

1. In medical apparatus for respiratory flow measurement, including a breathing tube for containing a fluid medium subject to respiratory flow varying at a breathing rate, and a flow measurement sensor accommodated in said breathing tube for coupling with the respiratory flow of the fluid medium in said breathing tube to control the supply of a respiratory flow signal as a function of such respiratory flow, said breathing tube having auxiliary means coupled with the fluid medium in said breathing tube for producing a supplementary flow component, supplementary measurement means responsive to the supplementary flow component to supply a supplementary signal which is dependent on a parameter of said fluid medium which also affects the accuracy of said respiratory flow signal, and evaluation means operatively connected with said flow measurement sensor and responsive to said respiratory flow signal and to said supplementary signal for forming a quotient signal as a function of the quotient of said respiratory flow signal and said supplementary signal to provide a respiratory flow indication compensated for said parameter of the fluid medium substantially independently of the type of respiratory gas or gases making up said fluid medium, said auxiliary means comprising a pump coupled with said fluid medium of said breathing tube for extracting a sample of said fluid medium from the breathing tube to produce said supplementary flow component, said supplementary measurement means comprising a supplementary flow measurement sensor coupled with said supplementary flow component to control the supply of said supplementary signal, and said evaluation means being operatively connected with said flow measurement sensor in said breathing tube to receive the respiratory flow signal controlled thereby and operatively connected with said supplementary flow measurement sensor for receiving said supplementary signal, and being operable for supplying said respiratory flow indication which is a function of the quotient of the respiratory flow signal and the supplementary signal.

2. Medical apparatus in accordance with claim 1, with said auxiliary means comprising an alternating pressure pump coupled with the fluid medium of said breathing the tube via said supplementary flow measurement sensor to produce said supplementary flow component at such supplementary flow measurement sensor.

3. Medical apparatus according to claim 1, with said supplementary measurement means being operable for supplying a supplementary signal wherein the contribution thereto due to the effect of said parameter at said supplementary flow measurement sensor has a magnitude substantially linearly proportional to the contribution to said respiratory flow signal due to the effect of said parameter at said flow measurement sensor in said breathing tube, the quotient of such signals thereby being essentially independent of such contributions substantially independently of the gas or gases making up said fluid medium.

4. Medical apparatus according according to claim 1, with said supplementary flow measurement sensor supplying a continuous analog signal which is to a substantial degree a predetermined function of the viscosity of the fluid medium, and said evaluation means supplying a respiratory flow indication which is substantially independent of the viscosity of the respiratory gas or gases forming said fluid medium.

5. Medical apparatus according to claim 1, with said supplementary flow measurement sensor supplying a continuous analog signal which is to a substantial degree a predetermined function of the density of the fluid medium, and said evaluation means being operable for supplying a respiratory flow indication which is substantially independent of the density of the respiratory gas or gases forming said fluid medium.

6. Medical apparatus according to claim 1, with said supplementary flow measurement sensor supplying a continuous analog signal which is to a substantial degree a predetermined function of the temperature conductivity of said fluid medium, and said evaluation means being operable for supplying a respiratory flow indication which is substantially independent of the temperature conductivity of the respiratory gas or gases forming said fluid medium.

7. In medical apparatus for respiratory flow measurement, including a breathing tube for containing a fluid medium subject to respiratory flow varying at a breathing rate, and a flow measurement sensor accommodated in said breathing tube for coupling with the respiratory flow of the fluid medium in said breathing tube to control the supply of a respiratory flow signal as a function of such respiratory flow, said breathing tube having auxiliary means coupled with the fluid medium in said breathing tube for producing a supplementary flow component, supplementary means responsive to the supplementary flow component to supply a supplementary signal which is dependent on a parameter of said fluid medium which also affects the accuracy of said respiratory flow signal, and evaluation means operatively connected with said flow measurement sensor and responsive to said respiratory flow signal and to said supplementary signal for forming a quotient signal as a function of the quotient of said respiratory flow signal and said supplementary signal to provide a respiratory flow indication compensated for said parameter of the fluid medium substantially independently of the type of respiratory gas or gases making up said fluid medium, said auxiliary means comprising a pump coupled with the fluid medium in said breathing tube for loading the respiratory flow so as to produce a supplementary flow component having a frequency which is capable of being differentiated from a breathing frequency of a breathing frequency signal component produced by the flow measurement sensor in response to said respiratory flow at said breathing rate, and said supplementary means being connected with said flow measurement sensor to receive therefrom a supplementary signal component having the frequency of said supplementary flow component, and being operable for separating said breathing frequency signal component and said supplementary signal component and for supplying a supplementary signal which is a function of said supplementary signal component as a separate input to said evaluation means, and said evaluation means being operable for supplying a respiratory flow indication which is a function of the quotient of such signal components so as to correct the respiratory flow signal in accordance with the composition and characteristics of the respiratory gas or gases forming said fluid medium.

8. Medical apparatus in accordance with claim 7, with said auxiliary means comprising an alternating pressure pump coupled with the fluid medium of said breathing tube and operating at a frequency which is capable of being differentiated from the breathing frequency corresponding to said breathing rate.

9. Medical apparatus according to claim 7, with a patient's mouthpiece for coupling respiratory flow to the fluid medium of the breathing tube, and flow resistance means providing a flow resistance of substantial magnitude between the mouthpiece and the breathing tube.

10. Medical apparatus according to claim 9, with said flow resistance means comprising a hose providing a flow path for said fluid medium of substantial length.

11. A medical apparatus according to claim 5, with said supplementary means comprising electronic filter means connected with said flow measurement sensor and tuned to the frequency of said supplementary flow component for separating the supplementary signal component from the breathing frequency signal component and for controlling the supplying of said supplementary signal to said evaluation means, and low-pass filter means coupled with said flow measurement sensor to receive therefrom said breathing frequency signal component and for controlling the supplying of said respiratory flow signal to said evaluation means.

12. Medical apparatus according to claim 11, with said supplementary means comprising band-pass electronic filter means connected with said flow measurement sensor and tuned to the frequency of said supplementary flow component for separating said supplementary signal component from said breathing frequency signal component, rectifier means connected with said band-pass filter means for rectifying said supplementary signal component, and low-pass filter means connected with said rectifier means for smoothing the output thereof and supplying an electrical supplementary signal for use in modifying said respiratory flow signal.

13. In medical apparatus for respiratory flow measurement, including a breathing tube for containing a fluid medium subject to respiratory flow varying at a breathing rate, and a flow measurement sensor accommodated in said breathing tube for coupling with the respiratory flow of the fluid medium in said breathing tube to control the supply of a respiratory flow signal as a function of such respiratory flow, said breathing tube having auxiliary means coupled with the fluid medium in said breathing tube for producing a supplementary flow component, supplementary means responsive to the supplementary flow component to supply a supplementary signal which is dependent on a parameter of said fluid medium which also affects the accuracy of said respiratory flow signal, and evaluation means operatively connected with said flow measurement sensor and responsive to said respiratory flow signal and to said supplementary signal for forming a quotient signal as a function of the quotient of said respiratory flow signal and said supplementary signal to provide a respiratory flow indication compensated for said parameter of the fluid medium substantially independently of the type of respiratory gas or gases making up said fluid medium, said auxiliary means comprising an alternating pressure pump coupled with the fluid medium and operable to provide a supplementary flow component in the form of a sinusoidal pulsation with a frequency substantially above the breathing frequency corresponding to said breathing rate.

14. Medical apparatus according to claim 13, with said alternating pressure pump producing a sinusoidal pulsation of a frequency between about 5 and about 15 hertz.

* * * * *